US011484595B2

(12) United States Patent
Tan et al.

(10) Patent No.: US 11,484,595 B2
(45) Date of Patent: Nov. 1, 2022

(54) CARRIER MOLECULE COMPOSITIONS AND RELATED METHODS

(71) Applicant: JYSK Skin Solutions PTE .LTD., Singapore (SG)

(72) Inventors: Siak-Khim Tan, Singapore (SG); Janifer Yeo-Tan, Singapore (SG)

(73) Assignee: JYSK Skin Solutions PTE. LTD., Singapore (SG)

( * ) Notice: Subject to any disclaimer, the term of this patent is extended or adjusted under 35 U.S.C. 154(b) by 0 days.

(21) Appl. No.: 15/841,059

(22) Filed: Dec. 13, 2017

(65) Prior Publication Data

US 2018/0214557 A1 Aug. 2, 2018

Related U.S. Application Data

(63) Continuation of application No. 14/963,155, filed on Dec. 8, 2015, now abandoned.

(60) Provisional application No. 62/088,813, filed on Dec. 8, 2014.

(51) Int. Cl.

| | |
|---|---|
| *A61K 38/10* | (2006.01) |
| *A61K 38/16* | (2006.01) |
| *A61K 38/00* | (2006.01) |
| *C07K 14/575* | (2006.01) |
| *A61P 23/00* | (2006.01) |
| *A61P 17/00* | (2006.01) |
| *A61P 29/00* | (2006.01) |
| *C07K 5/00* | (2006.01) |
| *C07K 7/00* | (2006.01) |
| *C07K 16/00* | (2006.01) |
| *C07K 17/00* | (2006.01) |
| *A61K 39/02* | (2006.01) |
| *A61K 39/08* | (2006.01) |
| *A61K 9/127* | (2006.01) |
| *A61K 47/42* | (2017.01) |
| *A61K 31/60* | (2006.01) |
| *A61K 38/48* | (2006.01) |
| *A61K 9/00* | (2006.01) |
| *A61K 9/107* | (2006.01) |
| *A61K 38/08* | (2019.01) |
| *C07K 14/33* | (2006.01) |
| *C07K 7/08* | (2006.01) |
| *A61P 25/00* | (2006.01) |
| *A61K 39/00* | (2006.01) |

(52) U.S. Cl.
CPC ............ *A61K 47/42* (2013.01); *A61K 9/0014* (2013.01); *A61K 9/107* (2013.01); *A61K 9/127* (2013.01); *A61K 31/60* (2013.01); *A61K 38/08* (2013.01); *A61K 38/10* (2013.01); *A61K 38/16* (2013.01); *A61K 38/4893* (2013.01); *A61K 39/08* (2013.01); *A61P 25/00* (2018.01); *A61P 29/00* (2018.01); *C07K 7/08* (2013.01); *C07K 14/33* (2013.01); *C12Y 304/24069* (2013.01); *A61K 2039/55516* (2013.01); *A61K 2039/55555* (2013.01); *A61K 2039/6031* (2013.01); *A61K 2039/6037* (2013.01); *A61K 2039/622* (2013.01); *C07K 2319/10* (2013.01)

(58) Field of Classification Search
None
See application file for complete search history.

(56) References Cited

U.S. PATENT DOCUMENTS

| | | | |
|---|---|---|---|
| 6,780,846 B1 * | 8/2004 | O'Mahony | A61K 9/1271 514/1.2 |
| 2006/0014712 A1 * | 1/2006 | Neuman | A61K 38/1709 514/44 A |
| 2008/0233152 A1 | 9/2008 | Waugh et al. | |
| 2009/0093026 A1 * | 4/2009 | Dowdy | C12N 15/111 435/375 |
| 2011/0212028 A1 * | 9/2011 | Ahmed | A61K 49/0004 424/9.1 |
| 2012/0195957 A1 | 8/2012 | Sachdeva | |
| 2014/0056811 A1 | 2/2014 | Etai et al. | |
| 2014/0335192 A1 * | 11/2014 | Ward | C12N 15/87 424/499 |
| 2016/0051646 A1 * | 2/2016 | Dake | A61P 25/06 424/94.67 |
| 2016/0166703 A1 | 6/2016 | Tan et al. | |

FOREIGN PATENT DOCUMENTS

| | | | | |
|---|---|---|---|---|
| WO | WO-02088318 A2 * | 11/2002 | | C12N 15/88 |
| WO | WO 2005/084410 A2 | 9/2005 | | |
| WO | WO 2006/094263 A2 | 9/2006 | | |
| WO | WO 2007/095152 A2 | 8/2007 | | |
| WO | WO 2010/039088 A1 | 4/2010 | | |
| WO | WO 2010/114828 A1 | 10/2010 | | |
| WO | WO 2016/092365 A1 | 6/2016 | | |

OTHER PUBLICATIONS

Sardan et al., Faraday Discuss. 166:269-283 (2013) (Year: 2013).*
"Nile Red", ThermoFisher Scientific, available online at https://www.thermofisher.com/order/catalog/product/N1142, 3 pages (accessed on May 24, 2017) (Year: 2017).*
"Carbohydrate", Biology Online, available online at http://www.biology-online.org/dictionary/Carbohydrate, 1 page (2008) (Year: 2008).*
See NCBI, PubChem Compound Database; CID=985, https://pubchem.ncbi.nlm.nih.gov/compound/985, 74 pages at pp. 4-6 (accessed on May 25, 2017) (Year: 2017).*

(Continued)

*Primary Examiner* — Thea D'Ambrosio

(74) *Attorney, Agent, or Firm* — McDermott Will and Emery LLP; Judy Mohr; Brett A. Schweers

(57) ABSTRACT

A carrier molecule composition. Specific implementations may include: a carrier molecule including at least one cell penetrating peptide (CPP) where the carrier molecule may include at least one hydrophobic domain and where the carrier is non-covalently associated with a biologically active molecule in one of a micelle and a liposome.

14 Claims, No Drawings

Specification includes a Sequence Listing.

(56) References Cited

OTHER PUBLICATIONS

Tung et al., Bioorgan. Med. Chem. 10:3609-3614 (2002) (Year: 2002).*
Klein et al., Prot. Eng. Des. Selection 27:325-330 (Oct. 2014) (Year: 2014).*
Lodish H, Berk A, Zipursky SL, et al. Molecular Cell Biology. 4th edition. New York: W. H. Freeman; 2000. Section 2.2, Noncovalent Bonds. Available from: https://www.ncbi.nlm.nih.gov/books/NBK21726/, 9 pages (Year: 2000).*
McKay et al., Holland-Frei Cancer Medicine, 6th Ed., Kufe et al., eds., BC Decker Inc., 9 pages (2003) (Year: 2003).*
"Carbohydrate", Biology Online, available online at http://www.biology-online.org/dictionary/Carbohydrate, 1 page (2008).
Desai et al., "(31)P Solid-state NMR based monitoring of permeation of cell penetrating peptides into skin", European Journal of Pharmaceutics and Biopharmaceutics, vol. 86, Issue 2, pp. 190-199 (2014).
International Search Report from PCT Patent Application No. PCT/IB2015/002430 dated May 17, 2016, application now published as International Publication No. WO2016/092365 on Jun. 16, 2016.
Klein et al., "Design and characterization of structured protein linkers with differing flexibilities", Protein Engineering Design & Selection, vol. 27, No. 10, pp. 325-330 (2014).
Lodish et al., "Section 2.2, Noncovalent Bonds", Molecular Cell Biology, 4$^{th}$ edition, New York: W.H. Freeman; 2000, available from: https://www.ncbi.nlm.nih.gov/books/NBK21726/, NCBI Bookshelf, 9 pages (2000).
"Nile Red", ThermoFisher Scientific, available online at https://www.thermofisher.com/order/catalog/product/N1142, Catalog No. N1142, 3 pages (accessed on May 24, 2017).
Pietz et al., "Ability of the hydrophobic FGF and basic TAT peptides to promote cellular uptake of recombinant Cre recombinase: a tool for efficient genetic engineering of mammalian genomes", Proc. Natl. Acad. Sci. USA, vol. 99, No. 7, pp. 4489-4494 (2002).
Sardan et al., "Cell penetrating peptide amphiphile integrated liposomal systems for enhanced delivery of anticancer drugs to tumor cells", Faraday Discussions, vol. 166, pp. 269-283 (2013).
"Palmitic Acid", Open Chemistry Database, PubChem CID: 985, accessed from: https://pubchem.ncbi.nim.nih.gov/compound/985, 74 pages at pp. 4-6 (accessed on May 25, 2017).
Tung et al., "Novel Branching Membrane Translocational Peptide as Gene Delivery Vector", Bioorganic Medicinal Chemistry, vol. 10, pp. 3609-3614 (2002).
Wang et al., "Preparation and evaluation of lidocaine hydrochloride-loaded TAT-conjugated polymeric liposomes for transdermal delivery", Int. J. Pharm., vol. 441, No. 1-2, pp. 748-756 (2013).
Wang et al., "Development of an efficient transdermal drug delivery system with TAT-conjugated cationic polymeric lipid vesicles", J. Mater. Chem. B, vol. 2, No. 7, pp. 877-884 (2014).

\* cited by examiner

SEQUENCE LISTING

```
<160> NUMBER OF SEQ ID NOS: 28

<210> SEQ ID NO 1
<211> LENGTH: 24
<212> TYPE: PRT
<213> ORGANISM: Artificial Sequence
<220> FEATURE:
<223> OTHER INFORMATION: Synthetic sequence
<220> FEATURE:
<221> NAME/KEY: MOD_RES
<222> LOCATION: (1)..(7)
<220> FEATURE:
<221> NAME/KEY: MOD_RES
<222> LOCATION: (8)..(17)
<223> OTHER INFORMATION: This region may encompass 0-10 Gly residues
<220> FEATURE:
<221> NAME/KEY: MOD_RES
<222> LOCATION: (18)..(24)

<400> SEQUENCE: 1

Phe Phe Phe Ile Leu Val Phe Gly Gly Gly Gly Gly Gly Gly Gly
1               5                   10                  15

Gly Lys Lys Arg Pro Lys Pro Gly
            20

<210> SEQ ID NO 2
<211> LENGTH: 23
<212> TYPE: PRT
<213> ORGANISM: Artificial Sequence
<220> FEATURE:
<223> OTHER INFORMATION: Synthetic sequence
<220> FEATURE:
<221> NAME/KEY: MOD_RES
<222> LOCATION: (1)..(6)
<220> FEATURE:
<221> NAME/KEY: MOD_RES
<222> LOCATION: (7)..(16)
<223> OTHER INFORMATION: This region may encompass 0 to 10 Gly residues
<220> FEATURE:
<221> NAME/KEY: MOD_RES
<222> LOCATION: (17)..(23)

<400> SEQUENCE: 2

Phe Leu Val Phe Phe Phe Gly Gly Gly Gly Gly Gly Gly Gly Gly
1               5                   10                  15

Lys Lys Arg Pro Lys Pro Gly
            20

<210> SEQ ID NO 3
```

```
<211> LENGTH: 23
<212> TYPE: PRT
<213> ORGANISM: Artificial Sequence
<220> FEATURE:
<223> OTHER INFORMATION: Synthetic sequence
<220> FEATURE:
<221> NAME/KEY: MOD_RES
<222> LOCATION: (1)..(7)
<220> FEATURE:
<221> NAME/KEY: MOD_RES
<222> LOCATION: (7)..(16)
<223> OTHER INFORMATION: This region may encompass 0-10 Gly residues
<220> FEATURE:
<221> NAME/KEY: MOD_RES
<222> LOCATION: (16)..(23)

<400> SEQUENCE: 3

Lys Lys Arg Pro Lys Pro Gly Gly Gly Gly Gly Gly Gly Gly Gly
1               5                   10                  15

Gly Phe Leu Val Phe Phe Phe
            20

<210> SEQ ID NO 4
<211> LENGTH: 7
<212> TYPE: PRT
<213> ORGANISM: Artificial Sequence
<220> FEATURE:
<223> OTHER INFORMATION: Synthetic sequence

<400> SEQUENCE: 4

Lys Lys Arg Pro Lys Pro Gly
1               5

<210> SEQ ID NO 5
<211> LENGTH: 28
<212> TYPE: PRT
<213> ORGANISM: Artificial Sequence
<220> FEATURE:
<223> OTHER INFORMATION: Synthetic sequence
<220> FEATURE:
<221> NAME/KEY: LIPID
<222> LOCATION: (1)..(1)
<223> OTHER INFORMATION: PALMITATE
<220> FEATURE:
<221> NAME/KEY: MOD_RES
<222> LOCATION: (2)..(21)
<223> OTHER INFORMATION: This region may encompass 0-20 Gly residues
<220> FEATURE:
<221> NAME/KEY: MOD_RES
<222> LOCATION: (22)..(28)

<400> SEQUENCE: 5

Xaa Gly Gly Gly Gly Gly Gly Gly Gly Gly Gly Gly Gly Gly Gly
1               5                   10                  15

Gly Gly Gly Gly Gly Lys Lys Arg Pro Lys Pro Gly
            20                  25

<210> SEQ ID NO 6
<211> LENGTH: 28
<212> TYPE: PRT
<213> ORGANISM: Artificial Sequence
<220> FEATURE:
<223> OTHER INFORMATION: Synthetic sequence
<220> FEATURE:
<221> NAME/KEY: LIPID
<222> LOCATION: (1)..(1)
<223> OTHER INFORMATION: OCTANOYL
<220> FEATURE:
<221> NAME/KEY: MOD_RES
<222> LOCATION: (2)..(21)
<223> OTHER INFORMATION: This region may encompass 0 to 20 Gly residues
```

```
<220> FEATURE:
<221> NAME/KEY: MOD_RES
<222> LOCATION: (21)..(28)
<223> OTHER INFORMATION: his region may encompass 0 to 20 Gly residues

<400> SEQUENCE: 6

Xaa Gly Gly Gly Gly Gly Gly Gly Gly Gly Gly Gly Gly Gly Gly
1               5                   10                  15

Gly Gly Gly Gly Gly Lys Lys Arg Pro Lys Pro Gly
            20                  25

<210> SEQ ID NO 7
<211> LENGTH: 28
<212> TYPE: PRT
<213> ORGANISM: Artificial Sequence
<220> FEATURE:
<223> OTHER INFORMATION: Synthetic sequence
<220> FEATURE:
<221> NAME/KEY: LIPID
<222> LOCATION: (1)..(1)
<223> OTHER INFORMATION: OLEYL
<220> FEATURE:
<221> NAME/KEY: MOD_RES
<222> LOCATION: (2)..(21)
<223> OTHER INFORMATION: This region may encompass 0 to 20 Gly residues
<220> FEATURE:
<221> NAME/KEY: MOD_RES
<222> LOCATION: (21)..(28)

<400> SEQUENCE: 7

Xaa Gly Gly Gly Gly Gly Gly Gly Gly Gly Gly Gly Gly Gly Gly
1               5                   10                  15

Gly Gly Gly Gly Gly Lys Lys Arg Pro Lys Pro Gly
            20                  25

<210> SEQ ID NO 8
<211> LENGTH: 51
<212> TYPE: PRT
<213> ORGANISM: Human immunodeficiency virus
<220> FEATURE:
<221> NAME/KEY: MOD_RES
<222> LOCATION: (1)..(20)
<223> OTHER INFORMATION: This region may encompass 0 to 20 Gly residues
<220> FEATURE:
<221> NAME/KEY: MOD_RES
<222> LOCATION: (21)..(31)
<220> FEATURE:
<221> NAME/KEY: MOD_RES
<222> LOCATION: (32)..(51)
<223> OTHER INFORMATION: This region may encompass 0 to 20 Gly residues

<400> SEQUENCE: 8

Gly Gly Gly Gly Gly Gly Gly Gly Gly Gly Gly Gly Gly Gly Gly
1               5                   10                  15

Gly Gly Gly Gly Arg Gly Arg Asp Asp Arg Gln Arg Arg Gly
            20                  25                  30

Gly Gly Gly Gly Gly Gly Gly Gly Gly Gly Gly Gly Gly Gly Gly
        35                  40                  45

Gly Gly Gly
    50

<210> SEQ ID NO 9
<211> LENGTH: 51
<212> TYPE: PRT
<213> ORGANISM: Human immunodeficiency virus
<220> FEATURE:
<221> NAME/KEY: MOD_RES
<222> LOCATION: (1)..(20)
```

```
<223> OTHER INFORMATION: This region may encompass 0 to 20 Gly residues
<220> FEATURE:
<221> NAME/KEY: MOD_RES
<222> LOCATION: (21)..(31)
<220> FEATURE:
<221> NAME/KEY: MOD_RES
<222> LOCATION: (32)..(51)

<400> SEQUENCE: 9

Gly Gly Gly Gly Gly Gly Gly Gly Gly Gly Gly Gly Gly Gly Gly
1               5                   10                  15

Gly Gly Gly Gly Tyr Gly Arg Lys Lys Arg Arg Gln Arg Arg Gly
            20                  25                  30

Gly Gly Gly Gly Gly Gly Gly Gly Gly Gly Gly Gly Gly Gly Gly
        35                  40                  45

Gly Gly Gly
    50

<210> SEQ ID NO 10
<211> LENGTH: 49
<212> TYPE: PRT
<213> ORGANISM: Human immunodeficiency virus
<220> FEATURE:
<221> NAME/KEY: MOD_RES
<222> LOCATION: (1)..(20)
<223> OTHER INFORMATION: This region may encompass 0 to 20 Gly residues
<220> FEATURE:
<221> NAME/KEY: MOD_RES
<222> LOCATION: (21)..(29)
<220> FEATURE:
<221> NAME/KEY: MOD_RES
<222> LOCATION: (30)..(49)
<223> OTHER INFORMATION: This region may encompass 0 to 20 Gly residues

<400> SEQUENCE: 10

Gly Gly Gly Gly Gly Gly Gly Gly Gly Gly Gly Gly Gly Gly Gly
1               5                   10                  15

Gly Gly Gly Gly Arg Lys Lys Arg Arg Gln Arg Arg Gly Gly Gly
            20                  25                  30

Gly Gly Gly Gly Gly Gly Gly Gly Gly Gly Gly Gly Gly Gly Gly
        35                  40                  45

Gly

<210> SEQ ID NO 11
<211> LENGTH: 9
<212> TYPE: PRT
<213> ORGANISM: Human immunodeficiency virus

<400> SEQUENCE: 11

Arg Arg Arg Arg Arg Arg Arg Arg Arg
1               5

<210> SEQ ID NO 12
<211> LENGTH: 15
<212> TYPE: PRT
<213> ORGANISM: Artificial Sequence
<220> FEATURE:
<223> OTHER INFORMATION: Antennapedia sequence

<400> SEQUENCE: 12

Arg Gln Ile Lys Trp Phe Gln Asn Arg Arg Met Lys Trp Lys Lys
1               5                   10                  15

<210> SEQ ID NO 13
<211> LENGTH: 38
```

```
<212> TYPE: PRT
<213> ORGANISM: Artificial Sequence
<220> FEATURE:
<223> OTHER INFORMATION: Transduction Domain 1

<400> SEQUENCE: 13

Asn Pro Gly Gly Tyr Cys Leu Thr Lys Trp Met Ile Leu Ala Ala Glu
1               5                   10                  15

Leu Lys Cys Phe Gly Asn Thr Ala Val Ala Lys Cys Asn Val Asn His
            20                  25                  30

Asp Ala Glu Phe Cys Asp
            35

<210> SEQ ID NO 14
<211> LENGTH: 26
<212> TYPE: PRT
<213> ORGANISM: Artificial Sequence
<220> FEATURE:
<223> OTHER INFORMATION: Melittin

<400> SEQUENCE: 14

Gly Ile Gly Ala Val Leu Lys Val Leu Thr Thr Gly Leu Pro Ala Leu
1               5                   10                  15

Ile Ser Trp Ile Lys Arg Lys Arg Gln Gln
            20                  25

<210> SEQ ID NO 15
<211> LENGTH: 12
<212> TYPE: PRT
<213> ORGANISM: Artificial Sequence
<220> FEATURE:
<223> OTHER INFORMATION: Prion

<400> SEQUENCE: 15

Ala Ala Val Leu Leu Pro Val Leu Leu Ala Ala Pro
1               5                   10

<210> SEQ ID NO 16
<211> LENGTH: 47
<212> TYPE: PRT
<213> ORGANISM: Artificial Sequence
<220> FEATURE:
<223> OTHER INFORMATION: Synthetic sequence
<220> FEATURE:
<221> NAME/KEY: MOD_RES
<222> LOCATION: (1)..(20)
<223> OTHER INFORMATION: This region may encompass 0 to 20 Gly residues
<220> FEATURE:
<221> NAME/KEY: MOD_RES
<222> LOCATION: (21)..(27)
<220> FEATURE:
<221> NAME/KEY: MOD_RES
<222> LOCATION: (28)..(47)
<223> OTHER INFORMATION: This region may encompass 0 to 20 Gly residues

<400> SEQUENCE: 16

Gly Gly Gly Gly Gly Gly Gly Gly Gly Gly Gly Gly Gly Gly Gly Gly
1               5                   10                  15

Gly Gly Gly Gly Lys Lys Arg Pro Lys Pro Gly Gly Gly Gly Gly Gly
            20                  25                  30

Gly Gly Gly Gly Gly Gly Gly Gly Gly Gly Gly Gly Gly Gly Gly
            35                  40                  45

<210> SEQ ID NO 17
<211> LENGTH: 7
<212> TYPE: PRT
```

```
<213> ORGANISM: Artificial Sequence
<220> FEATURE:
<223> OTHER INFORMATION: Synthetic sequence

<400> SEQUENCE: 17

Lys Lys Arg Pro Lys Pro Gly
1               5

<210> SEQ ID NO 18
<211> LENGTH: 8
<212> TYPE: PRT
<213> ORGANISM: Artificial Sequence
<220> FEATURE:
<223> OTHER INFORMATION: Synthetic sequence

<400> SEQUENCE: 18

Phe Leu Val Phe Phe Phe Gly Gly
1               5

<210> SEQ ID NO 19
<211> LENGTH: 45
<212> TYPE: PRT
<213> ORGANISM: Artificial Sequence
<220> FEATURE:
<223> OTHER INFORMATION: Synthetic sequence
<220> FEATURE:
<221> NAME/KEY: MOD_RES
<222> LOCATION: (1)..(20)
<223> OTHER INFORMATION: This region may encompass 0 to 20 Gly residues
<220> FEATURE:
<221> NAME/KEY: MOD_RES
<222> LOCATION: (21)..(45)
<223> OTHER INFORMATION: This region may encompass 5 to 25 Arg residues

<400> SEQUENCE: 19

Gly Gly Gly Gly Gly Gly Gly Gly Gly Gly Gly Gly Gly Gly Gly Gly
1               5                   10                  15

Gly Gly Gly Gly Arg Arg Arg Arg Arg Arg Arg Arg Arg Arg Arg Arg
            20                  25                  30

Arg Arg Arg Arg Arg Arg Arg Arg Arg Arg Arg Arg Arg
        35                  40                  45

<210> SEQ ID NO 20
<211> LENGTH: 47
<212> TYPE: PRT
<213> ORGANISM: Artificial Sequence
<220> FEATURE:
<223> OTHER INFORMATION: Synthetic sequence
<220> FEATURE:
<221> NAME/KEY: MOD_RES
<222> LOCATION: (1)..(20)
<223> OTHER INFORMATION: This region may encompass 0 to 20 Gly residues
<220> FEATURE:
<221> NAME/KEY: MOD_RES
<222> LOCATION: (21)..(27)
<220> FEATURE:
<221> NAME/KEY: MOD_RES
<222> LOCATION: (28)..(47)
<223> OTHER INFORMATION: This region may encompass 0 to 20 Gly residues

<400> SEQUENCE: 20

Gly Gly Gly Gly Gly Gly Gly Gly Gly Gly Gly Gly Gly Gly Gly Gly
1               5                   10                  15

Gly Gly Gly Gly Lys Lys Arg Pro Gln Pro Asp Gly Gly Gly Gly Gly
            20                  25                  30

Gly Gly Gly Gly Gly Gly Gly Gly Gly Gly Gly Gly Gly Gly Gly
        35                  40                  45
```

<210> SEQ ID NO 21
<211> LENGTH: 17
<212> TYPE: PRT
<213> ORGANISM: Artificial Sequence
<220> FEATURE:
<223> OTHER INFORMATION: Synthetic sequence

<400> SEQUENCE: 21

Lys Lys Arg Pro Lys Pro Gly Gly Gly Gly Phe Phe Phe Ile Leu Val
1               5                   10                  15

Phe

<210> SEQ ID NO 22
<211> LENGTH: 17
<212> TYPE: PRT
<213> ORGANISM: Artificial Sequence
<220> FEATURE:
<223> OTHER INFORMATION: Synthetic sequence

<400> SEQUENCE: 22

Phe Phe Phe Ile Leu Val Phe Gly Gly Gly Lys Lys Arg Pro Lys Pro
1               5                   10                  15

Gly

<210> SEQ ID NO 23
<211> LENGTH: 11
<212> TYPE: PRT
<213> ORGANISM: Artificial Sequence
<220> FEATURE:
<223> OTHER INFORMATION: Synthetic sequence

<400> SEQUENCE: 23

Gly Gly Gly Gly Lys Lys Arg Pro Lys Pro Gly
1               5                   10

<210> SEQ ID NO 24
<211> LENGTH: 20
<212> TYPE: PRT
<213> ORGANISM: Artificial Sequence
<220> FEATURE:
<223> OTHER INFORMATION: Synthetic sequence

<400> SEQUENCE: 24

Arg Lys Lys Arg Arg Gln Arg Arg Gly Gly Gly Gly Phe Phe Phe
1               5                   10                  15

Ile Leu Val Phe
            20

<210> SEQ ID NO 25
<211> LENGTH: 13
<212> TYPE: PRT
<213> ORGANISM: Artificial Sequence
<220> FEATURE:
<223> OTHER INFORMATION: Synthetic sequence

<400> SEQUENCE: 25

Gly Gly Gly Gly Arg Lys Lys Arg Arg Gln Arg Arg Arg
1               5                   10

<210> SEQ ID NO 26
<211> LENGTH: 6
<212> TYPE: PRT
<213> ORGANISM: Artificial Sequence
<220> FEATURE:
<223> OTHER INFORMATION: Synthetic sequence

```
<400> SEQUENCE: 26

Val Gly Val Ala Pro Gly
1               5

<210> SEQ ID NO 27
<211> LENGTH: 17
<212> TYPE: PRT
<213> ORGANISM: Artificial Sequence
<220> FEATURE:
<223> OTHER INFORMATION: Synthetic sequence

<400> SEQUENCE: 27

Phe Phe Phe Ile Leu Val Phe Gly Gly Gly Lys Lys Arg Pro Lys Pro
1               5                   10                  15

Gly

<210> SEQ ID NO 28
<211> LENGTH: 11
<212> TYPE: PRT
<213> ORGANISM: Human immunodeficiency virus

<400> SEQUENCE: 28

Gly Gly Arg Lys Lys Arg Arg Gln Arg Arg Arg
1               5                   10
```

CARRIER MOLECULE COMPOSITIONS AND RELATED METHODS

CROSS REFERENCE TO RELATED APPLICATIONS

This application is a continuation of U.S. application Ser. No. 14/963,155, filed Dec. 8, 2015, which claims the benefit of the filing date of U.S. Provisional Patent Application No. 62/088,813 entitled "Carrier Molecule Compositions and Related Methods" to Tan et al., which was filed on Dec. 8, 2014, (the '813 provisional), the disclosures of which are hereby incorporated entirely herein by reference.

SEQUENCE LISTING

This document contains the material in and hereby incorporates entirely herein by reference the sequence listing file in ASCII text format filed on Dec. 13, 2017 named 103092_0023seqlist.txt, created Dec. 12, 2017, which is 11,824 bytes in size.

BACKGROUND

1. Technical Field

Aspects of this document relate generally to compositions and methods used to deliver biologically active molecules. More specific implementations involve include compositions that are capable of delivering biologically active molecules transdermally.

2. Background

Biologically active molecules can carry out, participate in, or initiate various biochemical changes in a human or animal body. For example, botulinum toxin is a biologically active molecule that acts as a neurotoxin that can cause muscle paralysis and is used to treat wrinkles of the skin. Botulinum toxin is conventionally administered to the skin through injection. Additional background information regarding the structure of skin, wrinkles of the skin, treatment methods for wrinkles, and botulinum toxin may be found in the following references, the disclosures of each of which are hereby incorporated entirely herein by reference: Inlander, *Skin*, New York, N.Y.: People's Medical Society, p. 1-7 (1998); Benedetto, *International Journal of Dermatology*, V. 38, p. 641-655 (1999); Stegman et al., "The Skin of the Aging Face," *Cosmetic Dermatological Surgery*, 2nd ed., St. Louis, Mo.: Mosby Year Book: p. 5-15 (1990); Lamanna, *Science*, V. 130, p. 763-772 (1959); Baron et al., *Bailey & Scotts Diagnostic Microbiology*, St. Louis, Mo.: Mosby Year Book, p. 504-523 (1994); Carruthers and Carruthers, *Adv. Dermatol.*, V. 12, p. 325-348 (1997); Markowitz, *Hunters Tropical Medicine*, 7th Ed., Philadelphia: W. B. Saunders, p. 441-444 (1991); Schantz and Scott, *Biomedical Aspects of Botulinum*, New York: Academic Press, p. 143-150 (1981); and Scott, *Ophthalmol*, V. 87, p. 1044-1049 (1980).

SUMMARY

Implementations of compositions may include: a carrier molecule including at least one cell penetrating peptide (CPP) where the carrier molecule may include at least one hydrophobic domain where the carrier is non-covalently associated with a biologically active molecule in one of a micelle and a liposome.

Implementations of compositions may include one, all, or any of the following:

The carrier molecule may be amphiphilic.

The carrier molecule may include at least one carbohydrate moiety.

The carrier molecule may include at least one alkyl chain.

The carrier molecule may include at least three hydrophobic amino acids.

The carrier molecule may include at least one phenylalanine.

The carrier molecule may include palmitoyl-gly$_p$-KKRPKPG (SEQ ID NO: 5), octanoyl-gly$_p$-KKRPKPG (SEQ ID NO: 6), oleyl-gly$_p$-KKRPKPG (SEQ ID NO: 7) or any combination thereof, where p is an integer from 0 to 20.

The carrier molecule may be selected from the group consisting of FFFILVFgly$_p$-KKRPKPG (SEQ ID NO: 1), FL VFFF-gly$_p$-KKRPKPG (SEQ ID NO: 2), KKRPKPGgly$_p$-FL VFFF (SEQ ID NO: 3), or any combination thereof, where p is an integer from 0 to 10.

The at least one CPP may be selected from the group consisting of an HIV-TAT fragment selected from the group consisting of a fragment that has the formula (gly)$_p$R-GRDDRRQRRR-(gly)$_q$ (SEQ ID NO: 8), a fragment that has the formula (gly)$_p$YGRKKRRQRRR-(gly)$_q$ (SEQ ID NO: 9), a fragment that has the formula (gly)$_p$-RKKRRQRRR-(gly)$_q$ (SEQ ID NO: 10), wherein the subscripts p and q are each independently an integer from 0 to 20; KKRPKPG (SEQ ID NO: 17); AA VLLPVLLAAP (SEQ ID NO: 15), or any combination thereof.

The biologically active molecule may be selected from the group consisting of VGVAPG (SEQ ID NO: 26); palmitoyl-TTS; retinyl retinoate; retinoic acid; steroid and steroidal compounds; hydroquinone; hyalonuric acid; non-steroidal anti-inflammatory drugs (NSAIDs) including naproxen, ibuprofen, and acetaminophen; skin-tightening peptides; light activatable moieties and compounds; ultraviolet (UV) light absorbing, blocking, or reflecting compounds; vitamins; cholesterol; drugs which block, influence, or interfere with neurotransmitter (such as acetylcholine) function; or any combination thereof.

The biologically active molecule may be selected from the group consisting of a botulinum toxin serotype selected from the group consisting of A, B, C, D, E, F, and G; recombinant botulinum toxin; a modified botulinum toxin; a fragment of a botulinum toxin; or any combination thereof.

Implementations of a composition may include a biologically active molecule and a carrier molecule including at least one lipophilic domain and at least one CPP where the carrier molecule further includes at least one carbohydrate moiety, at least one alkyl chain, at least three hydrophobic amino acids, or any combination thereof. The carrier molecule and biologically active molecule may associated non-covalently.

Implementations of a composition may include one, all, or any of the following:

The carrier molecule may include palmitoyl-gly$_p$-KKRPKPG (SEQ ID NO: 5), octanoyl-gly$_p$-KKRPKPG (SEQ ID NO: 6), oleyl-gly$_p$-KKRPKPG (SEQ ID NO: 7) or any combination thereof, where p is an integer from 0 to 20.

The carrier molecule may be selected from the group consisting of FFFILVFgly$_p$-KKRPKPG (SEQ ID NO: 1), FL VFFF-gly$_p$-KKRPKPG (SEQ ID NO: 2), KKRPKPGgly$_p$-FL VFFF (SEQ ID NO: 3), or any combination thereof, where p is an integer from 0 to 10.

The at least one CPP may be selected from the group consisting of an HIV-TAT fragment selected from the group consisting of a fragment that has the formula (gly)$_p$R-

GRDDRRQRRR-(gly)$_q$ (SEQ ID NO: 8), a fragment that has the formula (gly)$_p$YGRKKRRQRRR-(gly)$_q$ (SEQ ID NO: 9), a fragment that has the formula (gly)$_p$RKKRRQRRR-(gly)$_q$ (SEQ ID NO: 10), wherein the subscripts p and q are each independently an integer from 0 to 20; KKRPKPG (SEQ ID NO: 17); AA VLLPVLLAAP (SEQ ID NO: 15), or any combination thereof.

The biologically active molecule may be selected from the group consisting of VGVAPG (SEQ ID NO: 26); palmitoyl-TTS; retinyl retinoate; retinoic acid; steroid and steroidal compounds; hydroquinone; hyaluronic acid; non-steroidal anti-inflammatory drugs (NSAIDs) including naproxen, ibuprofen, and acetaminophen; skin-tightening peptides; light activatable moieties and compounds; ultraviolet (UV) light absorbing, blocking, or reflecting compounds; vitamins; cholesterol; drugs which block, influence, or interfere with neurotransmitter (such as acetylcholine) function; or any combination thereof.

The biologically active molecule may be selected from the group consisting of a botulinum toxin serotype selected from the group consisting of A, B, C, D, E, F, and G; recombinant botulinum toxin; a modified botulinum toxin; a fragment of a botulinum toxin; or any combination thereof.

A kit for administration of botulinum toxin to a patient may include a botulinum toxin, an effective amount for transdermal delivery thereof of a carrier molecule including at least one CPP where the carrier molecule includes at least one hydrophobic domain. A pH buffer system adapted to maintain pH between 4.0 to 8.3 may be included along with a device including the botulinum toxin, the carrier molecule, and the pH buffer system. The device may be adapted to administer the botulinum toxin to a patient via the patient's skin. The carrier molecule may be non-covalently associated with the botulinum toxin in one a micelle and a liposome. The device, the carrier molecule, the pH buffer system, or any combination thereof may be adapted to provide a controlled release of the botulinum toxin.

Implementations of a kit may include one, all, or any of the following:

The device may be a skin patch.

The botulinum toxin, the carrier molecule, and the pH buffer system may be included in a liquid, gel, cream, lotion, and ointment coupled with the device.

The foregoing and other aspects, features, and advantages will be apparent to those artisans of ordinary skill in the art from the DESCRIPTION and DRAWINGS, and from the CLAIMS.

DESCRIPTION

This disclosure, its aspects and implementations, are not limited to the specific components, assembly procedures or method elements disclosed herein. Many additional components, assembly procedures and/or method elements known in the art consistent with the intended carrier molecule compositions, kits, and related method implementations will become apparent for use with particular implementations from this disclosure. Accordingly, for example, although particular implementations are disclosed, such implementations and implementing components may comprise any shape, size, style, type, model, version, measurement, concentration, material, quantity, method element, step, and/or the like as is known in the art for such carrier molecule compositions, kits, and related methods, and implementing components and methods, consistent with the intended operation and methods.

The skin is the largest organ of the body and includes various layers, including the epidermis and dermis. The epidermis consists of keratinocytes and is divided into several layers based on their state of differentiation. The epidermis can be further classified into the stratum corneum and the viable epidermis, which consists of the granular melphigian and basal cells. The stratum corneum is hygroscopic and requires at least 10% moisture by weight to maintain its flexibility and softness. The hygroscopicity is attributable in part to the waterholding capacity of keratin. When the horny layer loses its softness and flexibility it becomes rough and brittle, resulting in dry skin. The dermis the thickest of the three layers of the skin and contains most of the skin's structures, including various sweat and oil glands, hair follicles, nerve endings, and blood and lymph vessels. The major components of the dermis are collagen and elastin.

The pH of skin is normally between 5 and 6 due to the presence of amphoteric amino acids, lactic acid, and fatty acids from the secretions of the sebaceous glands. The term "acid mantle" refers to the presence of the water-soluble substances on most regions of the skin. The buffering capacity of the skin is due in part to these secretions stored in the skin's horny layer.

One of the principal functions of skin is to provide a barrier to the transportation of water and substances potentially harmful to normal homeostasis. The body would rapidly dehydrate without a tough, semi-permeable skin. The skin helps to prevent the entry of harmful substances into the body. Although most substances cannot penetrate the barrier, a number of strategies have been developed to selectively increase the permeability of skin with variable success.

As individuals age, their skin begins to wrinkle as the result of the operation of various factors including biochemical, histological, and physiologic changes that accumulate from environmental damage, the constant pull of gravity, and repeated facial movements caused by contraction of facial muscles.

Botulinum toxins (also known as botulin toxins or botulinum neurotoxins) are neurotoxins produced by the gram-positive bacteria *Clostridium botulinum*. Without being bound by any theory, they are believed act to produce flaccid paralysis of muscles by preventing synaptic transmission or release of acetylcholine across the neuromuscular junction, as well as via other mechanisms.

Botulinum toxin is classified into eight neurotoxins that are distinct but serologically related. Of these, seven can cause paralysis: botulinum neurotoxin serotypes A, B, C, D, E, F and G. The molecular weight of the botulinum toxin protein molecule for all seven of these active botulinum toxin serotypes is about 150 kilo Daltons (kD). As released by the bacterium, the botulinum toxins are complexes comprising the 150 kD botulinum toxin protein molecule in question along with associated non-toxin proteins. The complexes which have a molecular weight greater than about 150 kD are believed to contain a non-toxin hemaglutinin protein and a non-toxin and nonhemaglutinin protein. These two non-toxin proteins (which along with the botulinum toxin molecule comprise the relevant neurotoxin complex) may act to provide stability against denaturation to the botulinum toxin molecule and protection against digestive acids when toxin is ingested.

Because botulinum toxin is capable of producing muscle paralysis and interfering with synaptic transmissions, it can be effectively used to treat various cosmetic skin conditions such as wrinkles as well as other physical and neurological conditions. As used herein, a biologically active molecule is a molecule that, by non-limiting example, similarly to botulinum toxin, chemically interacts with the biological tissue and/or cells to produce a desired biological effect. Botulinum toxin is an example of a biologically active molecule. Other examples of biologically active molecules include retinoic acid, steroids, hydroquinone, hyaluronic acid, and non-steroidal anti-inflammatory drugs (NSAIDs) including acetaminophen, ibuprofen, and naproxen.

Implementations of compositions of carrier molecules that act to transport and/or facilitate transport of biologically active molecules into cells and other tissues are disclosed herein. Also disclosed are implementations of various kits containing various carrier molecule compositions and implementations of various methods of administering biologically active molecules using carrier molecule compositions.

Implementations of carrier molecules disclosed herein contain at least one lipophilic domain and at least one cell penetrating peptide. In various implementations, the lipophilic domain is a hydrophobic domain. The carrier molecule implementations are also designed so that the carrier molecule directly and/or non-covalently associates with one or more biologically active molecules. In particular implementations, carrier molecules associate noncovalently with one or more hydrophobic, lipophilic, or amphiphilic portions of another molecule. Such a molecule can be the biologically active molecule(s) or a part of a delivery system for the carrier molecules which contains the biologically active molecule(s).

In particular implementations, the carrier molecule compositions may be used on conjunction with a biologically active molecule which is a botulinum toxin. Such implementations may include those that enable the transport or delivery of a botulinum toxin through the skin or epithelium without the use of transcutaneous delivery via a needle or injection. These composition implementations may be used as topical applications for providing a botulinum toxin to a subject for various therapeutic, aesthetic and/or cosmetic purposes, as described herein.

In such implementations, the composition includes a botulinum toxin associated with a carrier molecule where carrier molecule has at least one lipophilic domain and/or hydrophobic domain and at least one cell penetrating protein/peptide (CPP). In these implementations, the association between the carrier molecule and the botulinum toxin is noncovalent. In various other implementations, the association between the carrier molecule and the biologically active molecule may be non-covalent as well. In particular implementations, the lipophilic domain may not be a polycation or polyanion. In various implementations, the lipophilic domain does not exert biologic activity itself but merely facilitates the transport of the biologically active molecule.

In various implementations, a wide variety of various molecules may be used as carrier molecules. The carrier molecules may have any of a wide variety of properties including being lipophilic or amphiphilic. In particular implementations, the carrier molecules may include a carbohydrate moiety. Examples of carbohydrate moieties that may be included in various implementations are, by non-limiting example, heptanoic acid, octanoic acid, palmitic acid, oleic acid, and any other fatty acid, fatty alcohol, or other carbohydrate compound, Implementations may also include at least one alkyl chain. In such implementations, the alkyl chain may include at least 5 carbons, have between 50 and 30 carbons, or have between 6 and 14 carbons. The alkyl chain may be fully or partially saturated. In implementations where the chain is only partially saturated, the carrier molecule implementations may include a mixture of cis/trans isomerized molecules or only the cis or only the trans isomer of the molecule.

Other carrier molecule implementations may include various combinations of amino acids. In some implementations, at least three hydrophobic amino acids may be employed. In such implementations, at least one of the amino acids may be phenylalanine. In other implementations, the carrier molecule may include at least 5 amino acids or at least 7 amino acids selected from the group consisting of valine (V), phenylalanine (F), alanine (A), glycine (G), praline (P), methionine (M), tryptophan (W), leucine (L), and isoleucine (I), and combination thereof, and any other hydrophobic amino acid. In other implementations, the carrier molecule may include at least 5 amino acids or at least 7 amino acids selected from the group consisting of cysteine (C), serine (S), tyrosine (Y), glutamine (Q), threonine (T), asparagine (N), glutamate (E), lysine (K), aspartic acid (D), arginine (R), and histidine (H), any combination thereof, and any other hydrophilic or polar amino acid. In some implementations, combinations of hydrophobic and hydrophobic, hydrophilic, and/or polar amino acids may be used. Also, other non-standard amino acids other than those listed may be utilized in various implementations.

In implementations of carrier molecules that include just amino acids, various combinations may be used. In various implementations, the carrier molecule may include a backbone selected from a peptidyl lipophilic polymeric backbone, peptidyl lipophilic oligomeric backbone, a nonpeptidyl lipophilic polymeric backbone, and a nonpeptidyl lipophilic oligomeric backbone.

As an example, the carrier molecule may be selected from FFFIL VF-gly$_p$KKRPKPG (SEQ ID NO: 1), FL VFFF-gly$_p$-KKRPKPG (SEQ ID NO: 2), KKRPKPG-gly$_p$FLVFFF (SEQ ID NO: 3), KKRPKPG (SEQ ID NO: 4), or any combination thereof, where p is an integer from 0 to 10. Sequence listings corresponding with these carrier molecule implementations along with sequence listings as indicated throughout this document may be in the Sequence Listing filed herewith, the disclosure of which is hereby incorporated entirely herein by reference. In various other carrier molecule implementations, various combinations of amino acids and palmitoyl, octanoyl, and oleyl groups may be utilized. For example, the carrier molecule may be one of palmitoyl-gly$_p$-KKRPKPG (SEQ ID NO: 5), octanoyl-gly$_p$-KKRPKPG (SEQ ID NO: 6), oleyl-gly$_p$-KKRPKPG (SEQ ID NO: 7), or any combination thereof, where p is an integer from 0 to 20.

In particular implementations, the carrier molecule includes a lipophilic oligo or polymeric backbone comprising at least one covalently bonded CPP. Any of a wide variety of CPPs may be employed in various composition implementations and in combination with various carrier molecule and active molecule implementations disclosed herein. One or more CPPs may be used, and may be included on the carrier molecule, active molecule, or both the carrier molecule and active molecule.

For example, the CPP may be an HIV fragment or HIV-TAT or HIV-TAT fragment. Example of such fragments include (gly)$_p$-RGRDDRRQRRR-(gly)$_q$ (SEQ ID NO: 8), a fragment that has the formula (gly)$_p$-YGRKKRRQRRR-(gly)q (SEQ ID NO: 9), a fragment that has the formula (gly)$_p$-RKKRRQRRR-(gly)$_q$ (SEQ ID NO: 10), and any combination of such fragments, where the subscripts p and q are each independently an integer from 0 to 20. In particular implementations, the HIV-TAT fragment may be specifically the SEQ ID NO: 10 version. In other implementations, the R9 CPP may be used, coded as RRRRRRRRR (SEQ ID NO: 11).

Other CPPs that may be included are Antennapedia, coded as RQIKWFQNRRMKWKK (SEQ ID NO: 12); Transduction Domain 1 (TD1) coded as NPGGYCLTKWMILAAELKCFGNTAV AKCNVNHDAEFCD (SEQ ID NO: 13); melittin, coded as GIGA VLKVLTTGL-PALISWIKRKRQQ (SEQ ID NO: 14); and prion, coded as AA VLLPVLLAAP (SEQ ID NO: 15). Other CPPs that may be employed include $(gly)_p$KKRPKPG-$(gly)_q$ (SEQ ID NO: 16) wherein the subscripts p and q are each independently an integer from 0 to 20; and KKRPKPG (SEQ ID NO: 17) standing alone. In particular implementations, the CPP may be FL VFFFGG (SEQ ID NO: 18). In other implementations the CPP may be -$(Gly)_{n1}$-$(Arg)_{n2}$ (SEQ ID NO: 19) or $gly_{n1a}$-KKRPQPD-$gly_{n1b}$ (SEQ ID NO: 20) where the subscript n1 is an integer of from 0 to about 20, subscripts n1a and n2a are each integers of from 0 to about 20, and the subscript n2 is an odd integer of from about 5 to about 25.

A wide variety of other CPPs from viral sources, including any homologous sequence from any virus capable of penetrating a human or animal cell wall, may be included and/or employed in various implementations. These may be any currently known or hereafter discovered consistent with the principles disclosed herein.

In addition, a wide variety of synthetic or otherwise man-made CPPs may be employed in various implementations. These may include one, a combination of all, or any combination of the following: KKRPKPGGGGFFFILVF (SEQ ID NO: 21), FFFIL VFGGGKKRPKPG (SEQ ID NO: 22), GGGGKKRPKPG (SEQ ID NO: 23), RKKRRQRRRGGGGFFFIL VF (SEQ ID NO: 24), and GGGGRKKRRQRRR (SEQ ID NO: 25). In particular implementations, GGGGKKRPKPG and GGG-GRKKRRQRRR may be bonded to a palmitoyl group to form the complete structure of the CPP and/or carrier molecule+CPP. The particular palmitoyl group used in various implementations of carrier molecules and CPPs disclosed herein may be n-palmitoyl.

A wide variety of biologically active molecules may be used in various implementations of compositions disclosed herein other than botulinum toxin actives. These include, by non-limiting example, VGV APG (SEQ ID NO: 26); palmitoyl covalently bonded to the TAT sequence disclosed herein as SEQ. NO. 10; retinyl retinoate; retinoic acid; steroid and steroidal compounds; hydroquinone; hyalonuric acid; non-steroidal anti-inflammatory drugs (NSAIDs) including naproxen, ibuprofen, and acetaminophen; skin-tightening peptides; light activatable moieties and compounds; ultraviolet (UV) light absorbing, blocking, or reflecting compounds; vitamins; cholesterol; drugs which block, influence, or interfere with neurotransmitter (such as acetylcholine) function; and any combination thereof.

A wide variety of composition implementations containing carrier molecules, CPPs, and biologically active molecules may be constructed using the principles disclosed herein. As an initial step, the carrier molecules are first prepared. Each carrier molecule may include one or more CPPs covalently bonded to it or otherwise associated with it. Following preparation of the carrier molecule/CPP combined molecule, the biologically active molecules are then associated non-covalently with the carrier molecule/CPP combined molecule. This may be done in a wide variety of ways, including, by non-limiting example, simple mixing, titrating, chelating, protein folding, incorporating into a liposome, incorporating into a nanoemulsion, direct associating, emulsifying, and any other technique for non-covalently associating the biologically active molecule with the carrier molecule/CPP combined molecule.

Particular implementations may be prepared for delivery via an emulsion or a liposomal preparation. Emulsion preparations involve those carrier molecules and/or CPPs that contain predominately hydrophilic or polar amino acids and involve adhering/associating the carrier molecules and/or CPPs (and correspondingly, the non-covalently bonded biologically active molecules) to a plurality of micelles in the emulsion. The emulsion may then be mixed with additional components contained in one or more liquid/solid phases to form a final composition adapted to be applied to a patient's skin.

Liposomal preparations may be used for those carrier molecules and/or CPPs that contain predominately hydrophobic amino acids. The combination of the carrier molecule, one or more CPPs, and one or more biologically active molecules is packaged into a liposome. The liposomes used in various implementations may be those from, and/or manufactured according to the processes and technologies used by Encapsula NanoSciences of Brentwood, Tenn.; Lippomix, Inc. of Novato, Calif.; Azaya Therapeutics Incorporated of San Antonio, Tex.; Oakwood Laboratories, L.L.C. of Oakwood Village, Ohio; Tergus Pharma of Durham, N.C. The respective disclosures of such liposomal compositions, and manufacture processes and technologies for each manufacturer are included in Appendices A, B, C, D, and E, to the '813 provisional, the disclosure of which was previously hereby incorporated entirely herein by reference. A plurality of liposomes are then prepared and mixed with additional components in one or more liquid/solid phases to form a final composition that also configured to be applied to patient's skin.

The final form of the composition implementations disclosed herein may take the form of a liquid, gel, cream, lotion, or ointment. The composition implementations may be stable when under room temperature storage and/or refrigerated storage. The compositions may have a pH from about 4.0 to about 8.3. In particular implementations, the composition may include a pH buffer system, which may include various components, including, by nonlimiting example, ascorbate, citrate, phosphate, any combination thereof, and any other pH buffering composition or compound. Particular composition implementations may be designed to provide a controlled and/or time delayed release of the biologically active molecule. This may be done in a variety of ways, including, by non-limiting example, causing a concentration-dependent reaction between the carrier molecule and/or CPP and a component of the skin to release the biologically active molecule, using a dissociation reaction with a particular activation energy between the biologically active molecule and the carrier molecule to drive a specific dissociation rate for the biologically active molecules, utilizing a combination of CPPs attached to various carrier molecules that have different reaction rates with skin cells to release biologically active molecules over time, and any other chemical reaction-driven, mass transport, or energy transport driven process designed to gradually release the biologically active molecules to the desired tissues in the skin.

Implementations of compositions like those disclosed herein may be included in a kit designed for administering the biologically active molecule to a subject. In particular implementations, the kit may be designed for administration of a botulinum toxin to a subject. The kit includes a botulinum toxin present in an effective amount for transdermal delivery thereof, and an implementation of carrier molecule like those disclosed herein that has at least one lipophilic domain and/or hydrophobic domain and at least one CPP where the association between the carrier and the botulinum toxin is non-covalent. Kit implementations include a device for delivering the botulinum toxin to the skin and a composition containing a carrier having at least one lipophilic domain and/or hydrophobic domain and at least one CPP. The particular carrier molecule and CPP(s) included in the composition may be any disclosed in this document.

Particular kits may include a kit component designed for preparing or formulating the composition that includes the carrier and the botulinum toxin, as well as such additional items that are needed to produce a usable formulation, or a premix that may in turn be used to produce such a formulation. In implementations, the kit contains a pre-formulated composition containing the carrier molecule and botulinum toxin; in other implementations, the kit contains a separately formulated botulinum toxin composition and a separately formulated carrier molecule composition. In other kit implementations, the kit includes materials for separately but in conjunction administering the botulinum toxin and the carrier molecule implementations to a subject's skin. The kit may also, in various implementations contain a device for administering the carrier molecule and/or botulinum toxin formulation to the subject via the subject's skin. In particular implementations, the device may be a skin patch.

Other components of the kit may include a device for administering the carrier molecule and biologically active molecule to the subject via the subject's skin. In particular implementations, the device may be a skin patch combined with one or more tubes containing the carrier molecule and/or biologically active molecule compositions. In particular kit implementations, the biologically active molecule may be a botulinum toxin. In other kit implementations, the biologically active molecule may be any disclosed in this document. Various kit implementations can include one or more wipes, one or more disinfectant wipes, one or more needles, one or more pumps, one or more sprayers, one or more tubes, and one or more applicator devices that may include, by non-limiting example, brushes, massagers, sonicators, and any other device for dermal application of a liquid or solid. Kit implementations may be designed for use by a health care professional or may be designed to allow a patient to self-administer them.

Compositions involving carrier molecules and biologically active molecules like those disclosed herein may be administered to a subject using a variety of implementations of a method of administering a particular biologically active molecule. For example, an implementation of a method of administering a botulinum toxin to a subject includes topically applying to the skin or epithelium of the subject the botulinum toxin in conjunction with an effective amount of a carrier molecule where the carrier molecule has at least one lipophilic domain and/or hydrophobic domain and at least one CPP, and is associated non-covalently with the botulinum toxin. The carrier molecule and at least one CPP may be any of those disclosed in this document. Other method implementations include producing a biologic effect such as muscle paralysis, softening skin, increasing luminosity of skin, tightening skin appearance, reducing hypersecretion or sweating, altering skin pigmentation, treating neurologic pain or migraine headache, reducing muscle spasms, preventing or reducing acne, or reducing or enhancing an immune response, by topically applying an effective amount of a composition containing a carrier molecule and biologically active molecule like those disclosed herein, preferably to the skin, of a subject or patient in need of such treatment. In addition, the method may include producing an aesthetic or cosmetic effect, for example, by topical application of botulinum toxin to the face instead of by conventional injection into facial muscles.

Example 1

An example of a topical preparation containing a carrier molecule and CPP along with a biologically active molecule was prepared and tested to determine its effect.
Table 1 outlines the experimental approach and results.

TABLE 1

| Component | Control (no carrier molecule) | Peptidyl Carrier | Palmitoyl Carrier |
|---|---|---|---|
| Large Molecular Weight | alkaline phosphatase conjugate | alkaline phosphatase conjugate | alkaline phosphatase conjugate |
| Small Molecular Weight | salicylate | salicylate | salicylate |
| Carrier Molecule | none | SK-2 (peptidyl-peptide) | SK-1 (palmitoyl-peptide) |
| Base | CETAPHIL ® moisturizer | CETAPHIL ® moisturizer | CETAPHIL ® moisturizer |

The alkaline phosphatase conjugate is an antibody weighting 150 kilodaltons. Additional saline only controls and saline in CETAPHIL® moisturizer base manufactured by Galderma Laboratories, LP. of Fort Worth, Tex. were prepared and tested as part of the experiment. The CETAPHIL® moisturizer base contained water, glycerin, petrolatum, dicaprylyl ether, dimethicone, glyceryl stearate, cetyl alcohol, *prunus amygdalus dulcis* (sweet almond) oil, PEG-30 stearate, tocopheryl acetate, acrylates/C I 0-30 alkyl acrylate crosspolymer, dimethiconol, benzyl alcohol, phenoxyethanol, methylparaben, propylparaben, glyceryl acrylate/acrylic acid copolymer, propylene glycol, disodium EDTA, and sodium hydroxide. The active and carrier molecules were added to the base via micelles. The SK-1 carrier molecule had the protein sequence of FFFIL VFGGGKKRPKPG (SEQ ID NO: 27) and the SK-2 carrier molecule had the protein sequence of palmitoyl-GGRKKRRQRRR (palmitoyl-TAT, SEQ ID NO: 28).

The experiment was conducted by selecting viable porcine skin grafts of thickness 0.045-0.055 inches that were freshly harvested, never frozen, and employed in replicates of n=5. Personnel were blinded to the identity of formulations to be applied to the surface of the skin. Receptor fluid applied to the skin grafts (0.9% NaCl) was collected for 14-16 hours after single time application of the formulation to each tested skin graft. Receptor fluid was pipetted to a 96 well plate in 200 microliter aliquots and tested in a spectrophotometer manufactured by Molecular Devices of Sunnyvale, Calif. Detection of salicylate was based on optical density (OD) reading and was conducted first. Afterward, an aliquot of 20 microliters per well of one step nitro-blue tetrazolium and 5-bromo-4-chloro-3'-indolyphosphate (NBT-BCIP) substrate was added to each well to visualize alkaline phosphatase activity. Timed serial measurements of the receptor fluid were employed to allow kinetic determination to confirm calculated concentration from standard curves (serial 1:3 dilutions from stock 150 kilodalton antibody-alkaline phosphatase conjugate solution).

The results of the experiment are summarized in Table 2:

TABLE 2

| SK-1 Active | SK-2 Active | No Carrier Control |
|---|---|---|
| 2.72916667 p < 0.01 by t-test | 2.660541667 p < 0.01 by t-test | 0.187792 |

When compared with standards, these absorbance numbers correspond to a calculated 1.8% transcutaneous flux of the biologically active molecules and carrier molecules in the micelle base using the SK-1 (palmitoyl-TAT CPP). The flux results of the two hydrophobic domain carrier molecules were not statistically different from one another, even across the widely different molecular weight biologically active molecules used for the testing. The experiment was replicated a second time and the results were similarly statistically significant enhanced flux of the biologically active molecules using the carrier molecules. That statistically significant flux enhancement for both large and small molecular weight compounds would be observed using the carrier molecules was an unexpected result, and indicates the effectiveness of using of a carrier molecule with a hydrophobic domain and CPP.

In places where the description above refers to particular implementations of carrier molecule compositions, kits, and related method implementations and implementing components, sub-components, methods and sub-methods, it should be readily apparent that a number of modifications may be made without departing from the spirit thereof and that these implementations, implementing components, sub-components, methods and sub-methods may be applied to other carrier molecule compositions, kits, and related method implementations.

What is claimed is:

1. A composition comprising:
a carrier molecule; and
a biologically active molecule,
wherein the carrier is non-covalently associated with the biologically active molecule in one of a micelle and a liposome, and
wherein the carrier molecule comprises one of FFFILVF-gly$_p$-KKRPKPG (SEQ ID NO: 1), FLVFFF-gly$_p$-KKRPKPG (SEQ ID NO: 2), KKRPKPG-gly$_p$-FLVFFF (SEQ ID NO: 3), or peptidyl-FFFILVFGGGKKRPKPG (SEQ ID NO: 27), or any combination thereof, and wherein p is an integer from 0 to 10.

2. The composition of claim 1, wherein the carrier molecule is amphiphilic.

3. The composition of claim 1, wherein the carrier molecule further comprises at least one fatty acid moiety.

4. The composition of claim 1, wherein the carrier molecule further comprises at least one alkyl chain.

5. The composition of claim 1, wherein the biologically active molecule is selected from the group consisting of VGVAPG (SEQ ID NO: 26); retinyl retinoate; retinoic acid; steroid and steroidal compounds; hydroquinone; hyalonuric acid; non-steroidal anti-inflammatory drugs (NSAIDs); light activatable moieties and compounds; ultraviolet (UV) light absorbing, blocking, or reflecting compounds; vitamins; cholesterol; drugs which block, influence, or interfere with neurotransmitter function; and any combination thereof.

6. The composition of claim 1, wherein the biologically active molecule is selected from the group consisting of: a botulinum toxin serotype selected from the group consisting of A, B, C, D, E, F, and G; recombinant botulinum toxin; a fragment of a botulinum toxin; and any combination thereof.

7. A composition comprising:
a biologically active molecule; and
a carrier molecule comprising at least one hydrophobic domain,
wherein the carrier molecule comprises one of FFFILVF-gly$_p$-KKRPKPG (SEQ ID NO: 1), FLVFFF-gly$_p$-KKRPKPG (SEQ ID NO: 2), KKRPKPG-gly$_p$-FLVFFF (SEQ ID NO: 3), or peptidyl-FFFILVFGGGKKRPKPG (SEQ ID NO: 27), or any combination thereof, wherein p is an integer from 0 to 10; and
the carrier molecule further comprising one of:
at least one fatty acid moiety;
at least one alkyl chain;
and
any combination thereof; and
wherein the carrier molecule and biologically active molecule associate non-covalently.

8. The composition of claim 7, wherein the biologically active molecule is selected from the group consisting of VGVAPG (SEQ ID NO: 26); retinyl retinoate; retinoic acid; steroid and steroidal compounds; hydroquinone; hyalonuric acid; non-steroidal anti-inflammatory drugs (NSAIDs); light activatable moieties and compounds; ultraviolet (UV) light absorbing, blocking, or reflecting compounds; vitamins; cholesterol; drugs which block, influence, or interfere with neurotransmitter function; and any combination thereof.

9. The composition of claim 7, wherein the biologically active molecule is selected from the group consisting of: a botulinum toxin serotype selected from the group consisting of A, B, C, D, E, F, and G; recombinant botulinum toxin; a modified botulinum toxin; a fragment of a botulinum toxin; and any combination thereof.

10. A kit for administration of a biologically active molecule to a patient, the kit comprising a device for delivering the biologically active molecule to the skin of the patient comprising the composition of claim 1.

11. The kit of claim 10, wherein the device is a skin patch.

12. The kit of claim 10, wherein the composition is comprised in a liquid, gel, cream, lotion, or ointment.

13. The kit of claim 10, wherein the biologically active molecule is selected from the group consisting of VGVAPG (SEQ ID NO: 26); retinyl retinoate; retinoic acid; steroid and steroidal compounds; hydroquinone; hyalonuric acid; non-steroidal anti-inflammatory drugs (NSAIDs); light activatable moieties and compounds; ultraviolet (UV) light absorbing, blocking, or reflecting compounds; vitamins; cholesterol; drugs which block, influence, or interfere with neurotransmitter function; and any combination thereof.

14. The kit of claim 10, wherein the biologically active molecule is selected from the group consisting of: a botulinum toxin serotype selected from the group consisting of A, B, C, D, E, F, and G; recombinant botulinum toxin; and any combination thereof.

* * * * *